(12) United States Patent
Sakamoto

(10) Patent No.: US 9,909,161 B2
(45) Date of Patent: Mar. 6, 2018

(54) METHOD AND SYSTEM FOR EVALUATION OF GRAFTS

(71) Applicant: Terumo Kabushiki Kaisha, Tokyo (JP)

(72) Inventor: Kenta Sakamoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 97 days.

(21) Appl. No.: 13/766,833

(22) Filed: Feb. 14, 2013

(65) Prior Publication Data

US 2013/0157305 A1   Jun. 20, 2013

Related U.S. Application Data

(63) Continuation of application No. PCT/JP2011/068587, filed on Aug. 17, 2011.

(30) Foreign Application Priority Data

Aug. 17, 2010   (JP) .................................. 2010-182142

(51) Int. Cl.
| | |
|---|---|
| *A61K 35/34* | (2015.01) |
| *C12Q 1/04* | (2006.01) |
| *C12N 5/077* | (2010.01) |
| *G01N 33/50* | (2006.01) |

(52) U.S. Cl.
CPC ............... *C12Q 1/04* (2013.01); *A61K 35/34* (2013.01); *C12N 5/0658* (2013.01); *G01N 33/5026* (2013.01); *G01N 2800/245* (2013.01)

(58) Field of Classification Search
None
See application file for complete search history.

(56) References Cited

U.S. PATENT DOCUMENTS

| | | | |
|---|---|---|---|
| 7,534,607 B1 * | 5/2009 | Chen et al. ................... | 435/377 |
| 2007/0092492 A1 | 4/2007 | Matsuda et al. | |

FOREIGN PATENT DOCUMENTS

| | | |
|---|---|---|
| JP | 2007-528755 A | 10/2007 |
| WO | 2006/122005 A2 | 11/2006 |
| WO | 2007/138577 A2 | 12/2007 |

OTHER PUBLICATIONS

Jankowski et al., Journal of Cell Science, vol. 115 (22), pp. 4361-4374, 2002.*
Suzuki et al., Cell Transplantation for the Treatment of Acute Myocardial Infarction Using VAscular Endothelial Growth Factor-Expressing Skeletal Myoblasts, Circulation, 2001; 104[suppl I]:I-207-I-212.*
RNeasy Mini Handbook, May 1999, Qiagen, pp. 22-44, retrieved from the internet: www.umich.edu/~caparray/PDF/RNeasy.pdf.*
Memon et al., Repair of impaired mycoardium by means of implantation of engineered autologous myoblast sheets, The Journal of Thoracic and Cardiovascular Surgery, vol. 130, No. 5, pp. 1333-1341.*
Memon et al., Journal of Thoracic and Cardiovascular Surgery, Sep. 2005, vol. 130, No. 3, pp. 646-653.*
"The Future of Microscopy All-In-One Digital Inverted microscope designed for performance and ease-of-use," issued by Advanced Microscopy Group (AMG), Mar. 24, 2010, retrieved from Internet on Jan. 17, 2014, http://www.mscience.com.au/upload/pages/amg/new-amg-evosfl-brochure-may10.pdf, (6 pages).
"Micron (EVOS) Digital Imaging Software User Guide," issued by Advanced Microscopy Group (AMG), Jul. 2, 2008, retrieved from Internet on Jan. 17, 2014, http://www.lifetechnologies.com/content/dam/LifeTech/Documents/PDFs/software-downloads/ugmicron.pdf, (38 pages).
Pagani et al., "Autologous Skeletal Myoblasts Transplanted to Ischemia-Damaged Myocardium in Humans, Histological Analysis of Cell Survival and Differentiation," Journal of the American College of Cardiology, Mar. 5, 2003, vol. 41, No. 5, pp. 879 to 888 (10 pages).
Herreros et al., "Autologous intramyocardial injection of cultured skeletal muscle-derived stem cells in patients with non-acute myocardial infarction", European Heart Journal, Nov. 1, 2003, vol. 24, No. 22, pp. 2012-2022 (9 pages).
Sim et al., "Cardiovascular and Vascular Regeneration, Skeletal Myoblast Transplant in Heart Failure", Jul. 18, 2003, http://onlinelibrary.wiley.com/store/10.1046/j.1540-8191.2003.02033.x/asset/j.1540-8191.2003.02033.x.pdf?v=1&t=hqrqxjij&s=97d95061cf4327868a3876aad983caa0ed6762a3 (9 pages).
Fukada., CD90-positive cells, an additional cell population, produce laminin α2 upon transplantation to $dy^{3k}/dy^{3k}$ mice, Experimental Cell Research, Academic Press, Dec. 1, 2007, vol. 314, No. 1, pp. 193-203 (9 pages).
Extended European Search Report and European Search Opinion issued in counterpart European Application No. 11 818 203.9, dated Jan. 30, 2014 (10 pages).
International Search Report from the International Bureau of WIPO for International Application No. PCT/JP2011/068587 dated Nov. 8, 2011 (2 pages) and English translation of the same (2 pages).
Yasuhiro Shudo et al., "Kingasaibo to Shibo Yurai Kan'yokei Saibo o Heiyo shita Saibo Sheet ni yoru Rat Manseiki Shinkinkosoku Model ni Taisuru Shinkin Saisei Kota no Kento", Gen. Thorac. Cardiovasc. Surg., Sep. 10, 2009, vol. 57, No. Supplement, p. 488.
Naozumi Sekiya et al., "Jiko Kingasaibo Sheet o Mochiita Shinkin Saisei Ryoho", Junkanki Senmon'i, Sep. 25, 2008, vol. 16, No. 2, pp. 245 to 251.
Mitsuhiro Saito et al., "Jusho Shinfuzen ni Taisuru Kokkakukin Kingasaibo Sheet Ishoku Chiryo no Kaihatsu", Inflamm. Ragen., Jul. 1, 2010, vol. 30, No. 4, p. 314.
Office Action dated Dec. 22, 2014 for European Patent Application No. 11 818 203.9. (7 pages).

(Continued)

*Primary Examiner* — Thane Underdahl
*Assistant Examiner* — Evelyn Y Pyla
(74) *Attorney, Agent, or Firm* — Fitch Even Tabin & Flannery LLP

(57) ABSTRACT

A method and system for evaluating the competence for transplantation of a graft sample containing cells capable of multinucleation are provided. In one form, the method includes determining multinucleating ability as an indicator representing the capacity for multinucleation of the cells capable of multinucleation.

9 Claims, 4 Drawing Sheets

(56) References Cited

OTHER PUBLICATIONS

Hoashi, Takaya, et al., "Skeletal Myoblast Sheet Transplantation Improves The Diastolic Function of a Pressure-Overloaded Right Heart." The Journal of Thoracic and Cardiovascular Surgery, Aug. 2009, vol. 138, No. 2, pp. 460-467.

Menasche, Philippe, et al., "The Myoblast Autologous Grafting in Ischemic Cardiomyopathy (MAGIC) Trial." Circulation, 2008, vol. 117, pp. 1189-1200.

* cited by examiner

FIG. 3
a)
b)
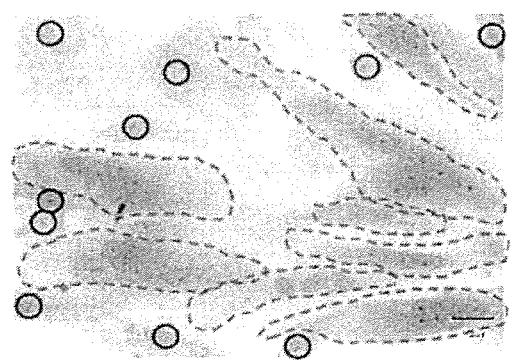
MEASUREMENT RESULTS
NUMBER OF MULTINUCLEATE CELLS (DOTTED LINE PORTIONS) = EIGHT

METHOD AND SYSTEM FOR EVALUATION OF GRAFTS

CROSS-REFERENCE TO RELATED APPLICATIONS

This application is a continuation of PCT/JP2011/068587 filed on Aug. 17, 2011, which claims priority from Japanese Patent Application JP 2010-182142, filed Aug. 17, 2010, which are hereby incorporated by reference in their entirety.

FIELD OF THE INVENTION

The present invention relates to a method and system for evaluation of competence for transplantation of a graft.

BACKGROUND OF THE INVENTION

Despite recent innovative progresses in the therapy of heart diseases, no firm therapeutic system has been established yet for severe heart failure. A common method for treating heart failure is that of medical therapy by means of β-blockers or an ACE inhibitor. Heart failure too severe to be effectively cured by such therapy is treated by replacement therapy with an auxiliary artificial heart or by heart transplantation, i.e., surgical therapy.

There are various causes for severe heart failure such that surgical therapy is needed. They include proceeded valvular disease, hyper myocardial ischemia, acute myocardial infarction and its complications, acute myocarditis, chronic cardiac failure due to ischemic myocarditis (ICM), dilated cardiomyopathy (DCM) or the like, and its acute oxacerbation.

Various techniques are applied to the foregoing diseases depending on their cause and severity. They include valvuloplasty, replacement, coronary artery bypass, left ventricular plasty, and mechanically assisted circulation.

It has been thought that the only way for effective treatment of cardiac failure resulting from the severely decreased function of left ventricle due to ICM and DCM is by replacement therapy involving heart transplantation and an artificial heart. However, replacement therapy for severe cardiac failure patients has many problems including a constant deficiency in the number of donors, the necessity for continuous immunosuppression, and various other complications. Therefore, it would be difficult to assert that replacement therapy is universally acceptable for treating severe cardiac failure.

In order to cope with the harsh situation surrounding heart transplantation, attempts were made for a short time to replace the foregoing surgical therapy by a new one such as the Batista operation procedure. This procedure attracted great attention as a substitute for heart transplantation. However, its limitations have recently been identified, and attempts are being made to improve this surgical procedure and its adequate application.

On the other hand, recently, the significance of the need for developing regenerative medicine as a new means for treating severe heart failure has been recognized.

Severe myocardial infarction or the like leads to incompetence of myocardial cells, which can further progress to the proliferation of fibroblasts and fibrosis of stroma, and eventually to heart failure. The progress of heart failure damages myocardial cells and leads to apotosis. As a result, myocardial cells, which undergo minimal cell division, decrease in number, thereby rendering the cardiac function even more incompetent.

It is considered that an effective way to reestablish healthy cardiac function for patients that have experienced severe heart failure is by cell transplantation. In fact, the transplantation of autoskeletal myoblasts has reached the stage of clinical application.

One example of the recent advancement of this technology is the production of three-dimensional cell cultures (for treating the heart) containing cells derived from any part of an adult other than their cardiac muscle, which has been realized by tissue engineering that employs temperature-responsive culture dishes. Such cell cultures and the method for production thereof have been disclosed Japanese Patent Laid-open No. 2007-528755.

SUMMARY OF THE INVENTION

It is an object of the present invention to provide a method for evaluating in a simple and accurate manner the competence for transplantation of a graft sample containing cells capable of multinucleation.

As mentioned above, a variety of grafts, particularly sheet-shaped cell cultures have been developed in order to address problems with cell transplantation in the field of regenerative medicine. However, the production of grafts for transplantation still involves technical difficulties and economical problems.

In the course of his investigation, the present inventor has encountered a new technical problem unknown before. The problem is that grafts prepared and transplanted in the same way differ from one another in the ratio of cell "take" and the state of cell growth into tissues. After his continued investigation to address this problem, the inventor found that the sheet-shaped cell cultures of skeletal myoblasts differ from one another in that one group of cells dissociated from the cell cultures yields more cytokine (which promotes the regeneration of cardiac muscles) than another group of cells if the former forms more fused cells than the latter during incubation in the culture medium. As a result of his extensive investigation, the inventor has completed the present invention.

Thus, the present invention relates to the following.

In one aspect, a method is provided for identifying graft samples that are competent for transplantation, with the method including: detecting a predetermined characteristic of cells from the graft samples that relate to the multinucleating ability of the cells; and selecting the graft samples for transplantation that have a predetermined level of multinucleating ability based on the detected predetermined characteristic.

The above method can include treating the graft samples prior to detecting the predetermined characteristic of the cells to allow the predetermined characteristic of the cells to be detected.

The above method can include dissociating individual cells from the graft samples, and incubating the dissociated individual cells prior to detecting the predetermined characteristic of the cells to allow the predetermined characteristic of the cells to be detected.

In the above method, the cells can be sheet-shaped cell cultures of skeletal myoblasts that are dissociated and incubated for detecting the predetermined characteristic thereof.

In the above method, the predetermined characteristic of cells can be detected by identifying multinucleate cells of the graft samples by at least one of visual observation and imaging.

The above method can include staining nuclei of the cells with a dye or fluorescent substance prior to identifying multinucleate cells by the at least one of visual observation and imaging.

In the above method, the predetermined characteristic of cells can be detected by detecting at least one of the number of multinucleate cells existing in each of the graft sample or a portion thereof; the rate of multinucleation in each of the graft samples or a portion thereof; the number of all nuclei existing in multinucleate cells in each of the graft samples or a portion thereof; the amount of cytokine yielded by each the graft samples or a portion thereof; and the amount of proteins held by each of the graft samples or a portion thereof.

In another aspect, a method is provided for identifying graft samples that are competent for transplantation, with the method including: obtaining individual cells from at least a portion of a graft sample; exposing the individual cells to predetermined conditions to encourage multinucleation; and detecting a predetermined characteristic of the cells related to the multinucleating ability of the cells in the graft sample.

In the above method, the individual cells can be obtained by dissociating a portion of one or not less than two graft samples into individual cells In the above method, the individual cells can be exposed to predetermined conditions by inoculating the individual cells onto a culture medium and incubating the individual cells under predetermined environmental conditions.

In the above method, the predetermined characteristic of the cells can be detected by directly measuring the number of multinucleating cells.

In the above method, the number of multinucleate cells can be directly measured by staining nuclei of the individual cells with a dye or fluorescent substance and identifying multinucleate cells by at least one of visual observation and imaging.

In the above method, the predetermined characteristic of the cells can be detected by staining the nuclei with a fluorescent substance, and sorting the cells having a fluorescent intensity that is at or above a predetermined level.

The above method can include determining the multinucleating ability of the graft sample by comparing the detected predetermined characteristic against at least one preset threshold value for the predetermined characteristic.

In the above method, determining the multinucleating ability of the graft sample can include at least one of determining at least one of the number of multinucleate cells, the rate of multinucleation, and the number of nuclei resulting from multinucleation.

The above method can include providing graft samples that are sheet-shaped cell cultures of skeletal myoblasts from which the individual cells are obtained and exposed to the predetermined conditions encouraging multinucleation.

In another aspect of the invention, a system for evaluating the competence of a graft sample for transplantation is provided, with the system including a detecting unit that is configured to analyze at least a portion of the graft sample and distinguish between multinucleate cells and other cells to classify the cells accordingly; and a calculating unit that is configured to receive and analyze the classification of the cells from the detecting unit and to determine the multinucleating ability of the graft sample.

In the above system, the detecting unit can be one of a flow cytometer device that is operable to classify the cells based on detecting a predetermined magnitude of signals from the nuclei of the cells, an imaging device that is operable to classify the cells based on distinguishing between staining of the nuclei and the cytoplasm of the cells, and a particle measuring device that is operated to measure particle size distribution of the cells that have undergone multinucleating treatment and been subsequently dissociated.

In the above system, the detecting unit can include an image analyzing unit configured to identify the number of multinucleate cells and the number of all cells in the portion of the graft sample, and the calculating unit can be configured to calculate the rate of multinucleation of the graft sample portion and compare the rate of multinucleation against at least one preset value for determining the multinucleating ability of the graft sample.

In the above system, the image analyzing unit can be configured to analyze different fields of view that meet predetermined conditions relating to cell and nuclei density for subsequent analysis for multinucleate cells. Other forms of the invention are discussed below.

(1) A method for evaluating the competence for transplantation of a graft sample containing cells capable of multinucleation, the method including:

determination of multinucleating ability as an indicator representing the capacity for multinucleation of the cells capable of multinucleation.

(2) The method as defined in paragraph (1) above, wherein the determination of the multinucleating ability includes:

(i) a step of dissociating a portion of one or not less than two graft samples into individual cells;

(ii) a step of incubating the dissociated cells obtained in step (i); and (iii) a step of detecting multinucleate cells in a cell culture obtained upon the incubation in step (ii), and the thus determined multinucleating ability is compared with a preset threshold value.

(3) The method as defined in paragraph (1) or (2) above, wherein the cells capable of multinucleation are skeletal myoblasts (muscle blast cells).

(4) The method as defined in any one of paragraphs (1) to (3) above, wherein the multinucleating ability is rate of multinucleation.

(5) The method as defined in any one of paragraphs (1) to (3) above, wherein the graft sample is determined as competent for transplantation to a living body where the cells capable of multinucleation are skeletal myoblasts and the rate of multinucleation as the multinucleating ability to be determined is higher than a preset threshold value.

(6) A system for evaluation of competence for transplantation of a graft sample containing cells capable of multinucleation, the system including:

a detecting unit which detects multinucleate cells; and a calculating unit which calculates the multinucleating ability.

(7) The system as defined in paragraph (6), wherein the detecting unit has an image analyzing unit which obtains and analyzes a cell image.

(8) The system as defined in paragraph (7) above, wherein the image analyzing unit has an imaging unit which obtains an image of stained cells, and the analysis by the image analyzing unit includes distinguishing between a cell region and a cell nucleus region in the cell image obtained by the imaging unit.

The present invention makes it possible to easily select from graft samples those which have a high ratio of take and are capable of growing into tissues. As a result, it will improve the effect of regenerative medicine by graft transplantation. Moreover, the method for evaluation according to the present invention makes it possible to consistently produce high-quality grafts in producing the grafts. In addition, the system for detecting multinucleate cells which can be used for the method according to the present invention makes it possible to detect multinucleate cells simply and easily, thereby improving the accuracy of evaluation according to the present invention.

BRIEF DESCRIPTION OF THE DRAWINGS

FIG. 3a) is an image showing skeletal myoblasts which have undergone multinucleation. This image was obtained by the system according to one embodiment of the present invention. FIG. 3b) is an image showing multinucleated cells detected in the image shown in FIG. 3a) according to one embodiment of the present invention. This image was obtained by distinguishing the image shown in FIG. 3a) into cell regions and further distinguishing the cell regions into nucleus regions. Each of the closed cell regions is examined for the number of closed nucleus regions existing therein. The cell region having a plurality of nucleus regions is recognized as a multinucleate cell. In the case shown in FIG. 3b), the number of multinucleate cells is eight.

DETAILED DESCRIPTION OF THE PREFERRED EMBODIMENTS

Figure 1:
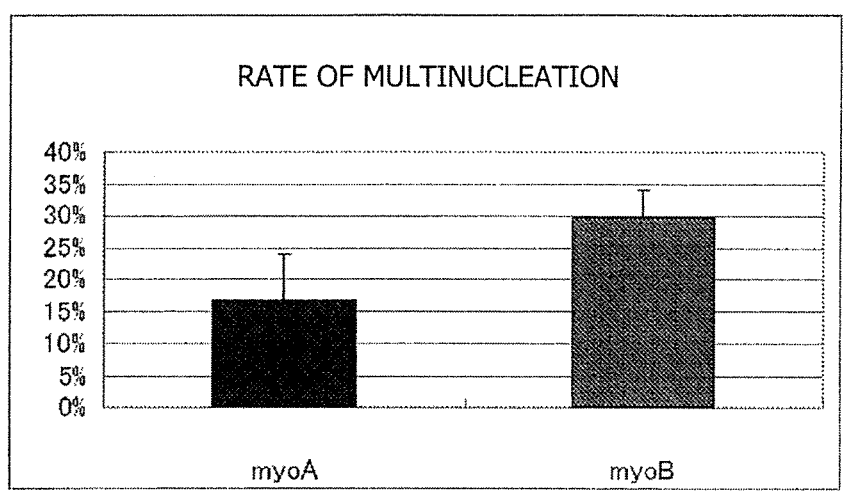
FIG. 1 is a diagram illustrating the rate of multinucleation of two kinds of skeletal myoblasts (myo A and myo B). It is noted that myo B has a higher rate of multinucleation than myo A.

The present invention relates to a method for evaluation of competence for transplantation of a graft sample containing cells capable of multinucleation, the method including determination of multinucleating ability as an indicator representing the capacity for multinucleation of the cells capable of multinucleation.

The graft sample for transplantation that is used in the present invention typically includes cultured cells and/or matter produced by them. It also includes various materials that fill and/or support specific parts (e.g., affected areas) of a living body (filling material and/or supporting material). Typically, it finds use for treatment of diseases and wounds of mammals, such as human and domestic animals, which are nonlimitative examples. The graft sample is not specifically restricted in its shape; it may assume shapes such as sheet, membrane, lump, and column shapes. The term "graft sample" used in the present invention may imply a piece of graft or a group of grafts. The group of grafts typically but unrestrictedly means a group of grafts from one lot.

The term "multinucleation" used herein means a transition to a state in which a single cell contains a plurality of cell nuclei. Possible causes for multinucleation include fusion, cell division, fragmentation of DNA in nucleus, incorporation of cells or nuclei, and differentiation. Therefore, "multinucleation" in the present specification denotes a transition to a state in which a single cell contains a plurality of cell nuclei whatever its cause may be. Thus, the term "multinucleate cell" implies any cell that has a plurality of cell nuclei. This term embraces "coenocyte" and "syncytium (also called fused cell)" which are terminologically distinguished in the technical field concerned. The former denotes those cells having a plurality of nuclei which occur in protozoa and fungi. The latter denotes those cells having a plurality of nuclei which occur in insects and animals. Syncytia (fused cells) are desirable because they can be contained in graft samples.

The term "competence for transplantation" as used in the present specification means the degree of competence of the graft sample for transplantation. Graft samples may be classified in any way according to their competence for transplantation. They may be divided into two classes, one which comes up to the standards being competent and the other which falls short of the standards being incompetent, for example. Alternatively, they may be divided into several classes which are ranked according to their competence for transplantation.

The term "multinucleating ability" as used herein denotes an indicator for numerical comparison of the capacity for multinucleation of cells in the graft sample in question, which expresses a characteristic of the graft sample. In the present invention, the multinucleating ability obtained from a portion of a graft sample is regarded as representing the multinucleating ability of the entire sample. The multinucleating ability may be expressed in any term reflecting the capacity for multinucleation of cells in the sample. For example, some unrestricted examples of such term include: the number of multinucleate cells existing in the sample after treatment of a part of the sample; the rate of multinucleation of cells capable of multinucleation in the sample after treatment; the number of all nuclei existing in multinucleate cells in the sample after treatment; the average number of nuclei of cells in the sample; the amount of cytokine yielded; the amount (and any numerical value equivalent thereto) of proteins (for example, creatinine kinase, desmin, myosin, and actin) held by the sample after treatment; and any numerical value which can be regarded as equivalent to these terms.

The present invention has been completed based on the present inventor's new finding that the multinucleating ability mentioned above can be used as the standard for evaluating the competence for transplantation of graft samples.

In the present invention, the multinucleating ability may be obtained in any way. It may vary depending on the specific object for measurement, such as the number of multinucleate cells after treatment for multinucleation or the average number of nuclei in cells in the sample after treatment for multinucleation. It may be obtained from samples by direct measurement or from the characteristic values of samples by calculations. The measurement of sample's characteristic values may be preceded by special treatment for measuring the characteristic values, such as multinucleation of cells in a sheet-shaped cell culture, which is useful in the case of evaluating the sheet-shaped cell cultures of skeletal myoblasts according to the method of the present invention. The measurement may be an invasive one or a non-invasive one.

In one embodiment of the present invention, the measurement of multinucleating ability is performed after the treatment for multinucleation. Specifically, the measurement of multinucleating ability includes:

(i) a step of dissociating a portion of one or not less than two graft samples into individual cells;

(ii) a step of incubating the dissociated cells obtained in step (i); and (iii) a step of detecting multinucleate cells in a cell obtained upon the incubation in step (ii).

In step (i) above, a portion of the graft sample is dissociated into individual separate cells. Dissociation can be achieved by any method well-known to those skilled in the art. A typical but non-limitative example of the method is treatment with trypsin. It is desirable that the treatment in step (i) should impose a minimum damage to cells so that it has little affect on the following step.

In step (ii) above, the dissociated separate cells obtained in step (i) are inoculated onto a culture medium and incubated. In such a step, the dissociated separate cells undergo multinucleation. Therefore, the culture medium on which to inoculate the cells may be any one that can be used for culture of cells. Preferably, however, a culture medium which includes an element which can accelerate multinucleation is used. The incubation may be carried out under any condition known in the technical field concerned. A typical but non-limitative condition is a temperature of 37° C. and a $CO_2$ concentration of 5%.

In step (iii) above, multinucleate cells in the cell culture obtained by incubation in step (ii) are detected. The detection of multinucleate cells can be performed by any method known in the technical field concerned. A typical example of an applicable method includes staining nuclei with a dye or a fluorescent substance and then identifying multinucleate cells by visual observation and/or imaging. Another example includes staining nuclei with a fluorescent substance and then sorting those cells having fluorescent intensity not lower than a prescribed level by using a cell sorter, such as flow cytometer (FCM). These methods are non-limitative examples.

By step (iii) above, multinucleate cells are detected and the multinucleating ability is determined thereby. For example, the number of multinucleate cells, the rate of multinucleation, and the number of nuclei resulting from multinucleation can be determined, which are non-limitative of the present invention. The multinucleating ability thus obtained is compared with a preset threshold value. The number of threshold values and the numerical value of each threshold value may vary according to the kind and degree of the multinucleating ability and evaluation to be determined. For instance, where the rate of multinucleation is adopted as the multinucleating ability, a judgment may be made that any sample having a higher rate of multinucleation is more desirable, which is non-limitative of the present invention. Also, where the evaluation is made in five grades, four threshold values may be used.

The threshold value may be determined in any way. For example, it may be set empirically, or it may be determined by treating one or not less than two reference samples in the same manner as the foregoing steps, measuring the multinucleating ability, and statistically processing the multinucleating ability thus obtained, which is non-limitative of the present invention.

The "cells capable of multinucleation" in the present invention may be any cells so long as they can be used for the graft sample. They are typically those cells which are capable of differentiation into skeletal muscle, although the present invention is not limited to this. In one embodiment of the present invention, the cells capable of multinucleation are preferably skeletal myoblasts from the standpoint of their usefulness in the regenerative medicine with grafts, their ease of cell cultivation and graft preparation, and their ability to provide prepared grafts high handleability and effectiveness.

The multinucleating ability may be expressed by any parameter that reflects the capacity for multinucleation of cells in the sample. In one embodiment of the present invention, the rate of multinucleation is used as the parameter from the viewpoints of ease and accuracy of measurement, etc. The term "rate of multinucleation" used herein represents the proportion of the number of multinucleated cells based on the total number of cells in the sample which has undergone treatment for multinucleation for the cells in the sample. The foregoing rate may include any rate (or proportion) which is regarded as equivalent to it. Therefore, the rate of multinucleation may be calculated from the number of all cells and the number of multinucleated cells in the sample. Alternatively, it may be obtained by averaging several values of the rate of multinucleation in one or not less than two randomly selected portions, for example.

The present invention will be described in more detail below with reference to one embodiment thereof, which is not restrictive of the invention.

In the embodiment of the present invention, a sheet-shaped cell culture of skeletal myoblasts is evaluated. Recently, skeletal myoblasts are considered to be useful for transplantation in the heart regenerative medicine. The sheet-shaped cell culture originating from the skeletal myoblasts is used as a graft for this purpose.

Evaluation of the sheet-shaped cell culture starts with its dissociation into individual separate cells. The dissociated cells are inoculated and incubated. After incubation for a predetermined period of time, the cells are observed under a microscope, with their nuclei and cytoplasm stained, so that the number of multinucleated cells and the total number of cells are counted. The procedure for observation and counting is repeated for several fields of view, and the rate of multinucleation is calculated. The rate of multinucleation thus obtained is compared with the preset threshold value. Those samples which have a rate of multinucleation higher than the preset threshold value can be regarded as suitable for transplantation to the heart.

In the method of the present invention, it is highly preferable that the detection of multinucleate cells should be performed speedily, simply, uniformly, and accurately. Therefore, the present invention covers a system for evaluation of competence for transplantation of graft samples containing cells capable of multinucleation. The system includes a detecting unit which detects multinucleate cells and a calculating unit which determines the multinucleating ability. The system configured in this manner is able to detect multinucleate cells more objectively and to make a more accurate evaluation. It also permits the evaluation of the present invention to be carried out speedily and simply.

The detecting unit mentioned above is not specifically restricted in its system design so long as it is able to distinguish between multinucleate cells and any other cells.

Unrestricted examples of the applicable system (system design) include: a system which is so designed as to classify cells by FCM according to the index defined by the magnitude of signals from the nucleus in one cell; a system which is so designed as to distinguish between multinucleate cells and any other cells by picking up an image of cells, with their nuclei and cytoplasm stained, and analyzing the resulting cell image; and a system which is designed so as to again dissociate the cells which have undergone multinucleating treatment into individual separate cells and measure the particle size distribution. These systems may be combined with one another. The result of classification made by the detecting unit is outputted to the calculating unit.

The outputting to the calculating unit may be accompanied by the outputting to a recording/outputting unit that outputs the result of classification. Examples of the recording unit include a recording medium such as hard disk and flash memory and printer. Examples of the outputting unit include a display monitor, a previously registered mobile phone and an internet address. Any other recording and outputting units known to those skilled in the art may be used unrestrictedly. The detecting unit may also be provided with an input unit for entry of detecting conditions, etc. Non-limitative examples of the input unit include a keyboard, a bar code reader, and a touch panel. Any input units known to those skilled in the art can be used.

The calculating unit is intended to analyze the result of classification which has been inputted from the detecting unit and then calculate the multinucleating ability. For example, it calculates the multinucleating ability, such as the rate of multinucleation, based on the information about FCM which has been inputted from the detecting unit, the information about multinucleate cells and any other cells classified by the image analysis, and the information about the particle size distribution resulting from particle size analysis. The calculating unit may have an input unit through which to enter the conditions for calculations and a recording/outputting unit by which to record and output the results of calculations. These units may be shared by the detecting unit. Further, the calculating unit may perform the comparison with the preset threshold values. Such threshold value may be one which is preliminarily recorded in the recording unit or one which is entered before examination or one which is a statistical value obtained from the results of past examinations in a feedback manner.

In one embodiment of the present invention, the detecting unit preferably has an image analyzing unit, from the viewpoint that a variety of information about cells can be obtained and a more direct and accurate analysis can be made thereby. In the case in which the detecting unit is the image analyzing unit, one embodiment of the system for analyzing the obtained image is described below, although the present invention is not limited to this. In the following description, it is assumed that the nuclei and cytoplasm in cells are stained by any one of staining methods known to those skilled in the art, such as fluorescent staining, DAPI staining, Hoechst staining, immunostaining, and Giemsa staining, for example.

Figure 4:
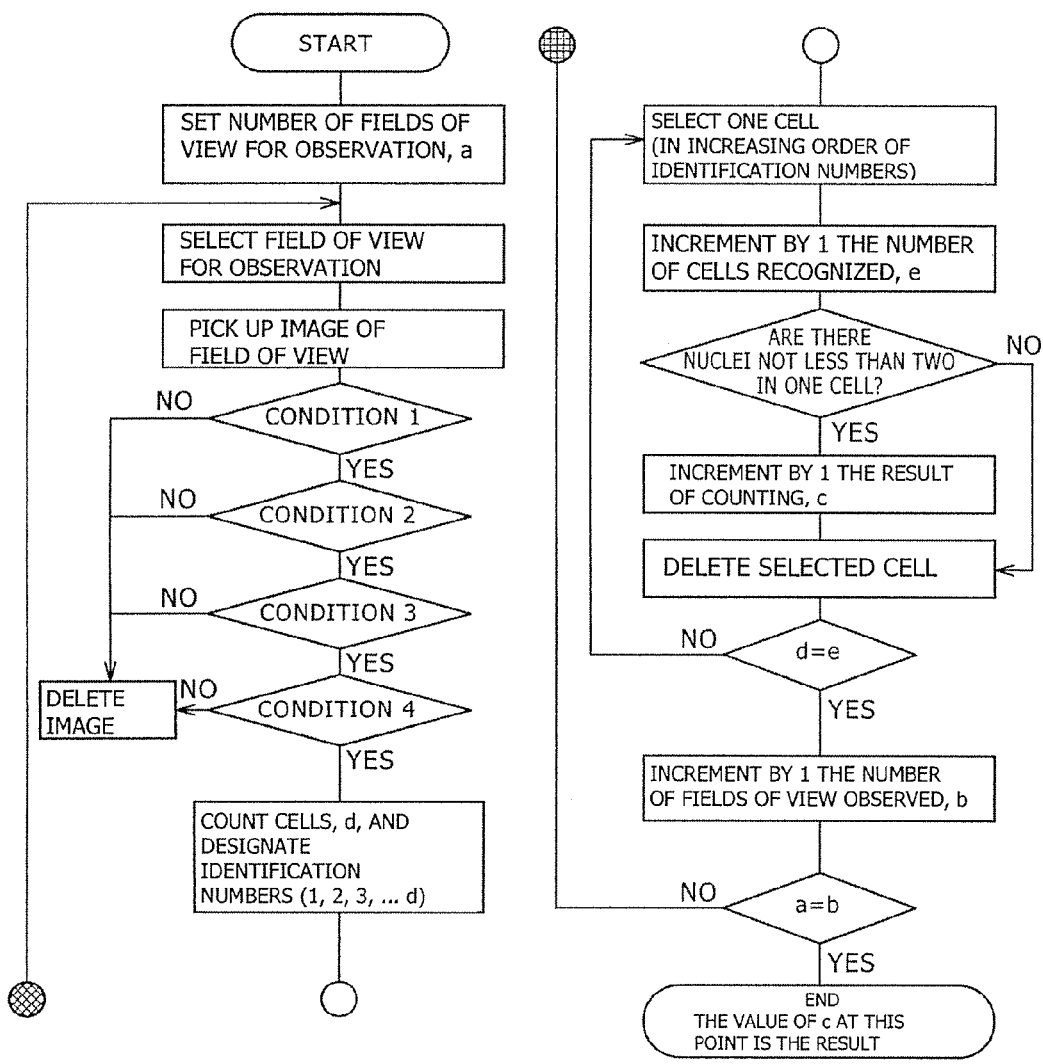
FIG. 4 is a flow diagram showing the image analyzing process by the system according to the present invention. The process was carried out under the following conditions.
Condition 1: The number of nuclei in the image is not more than 100.
Condition 2: The number of nuclei in the image is not less than one.
Condition 3: The region containing no cells accounts for less than 50% of the total area of the image.
Condition 4: In the image, there exists no region that contains no cells and there exists no region that is other than cyptoplasm and nucleus.

One embodiment of the flow of the image analysis process in the present invention is shown in FIG. 4. In this embodiment, first, the number of fields of view, (a), for observation of the sample placed in the detecting unit is set. The set point may be one which is recorded in the recording unit or one which is entered through the input unit. The next step is to select the field of view for observation and pick up an image of the field of view by using the imaging unit. The picked-up images are divided into a first group which meets all of the following conditions and a second group which does not meet all of the following conditions.

Condition 1: The number of nuclei in the image is not more than 100.
Condition 2: The number of nuclei in the image is not less than one.
Condition 3: The region containing no cells accounts for less than 50% of the total area of the image.
Condition 4: In the image, there exists no region that contains no cells and there exists no region that is other than cytoplasm and nucleus.

The images belonging to the first group are accepted for analysis and the other images belonging to the second group are discarded (deleted), and the next field of view is imaged. Incidentally, in this embodiment, the nuclei and cytoplasm in the same cell can be stained separately.

The image analyzing step proceeds in the following way. First, the segments of cytoplasm are distinguished as the cell regions (cellular region). The cell regions are given identification numbers, 1 to (d), sequentially. Next, the cell region having the smallest identification number is selected. The number of cells observed, (e), is incremented by 1. The segments of nuclei in the cell region are detected as the nucleus regions. If there are two or more nucleus regions in the cell region, the result of counting, (c), is incremented by 1. Thereafter the selected cell is deleted, and the number of cells observed, (e), and the identification number, (d), are compared with each other. If d=e, a determination is made that all the cells in the field of view have been recognized, and the number of fields of view observed, (b), is incremented by 1. If d=e is not satisfied, the control process returns to the cell region selecting step, to again select the cell regions in the increasing order of the identification number. This procedure is repeated until the result becomes d=e. Finally, the number of fields of view, (b), and the number of fields to be observed, (a), are compared with each other, and the analysis is stopped if a=b. If a=b is not satisfied, the next field of view is observed. This procedure is repeated until the result becomes a=b.

The foregoing analysis gives the number of multinucleate cells in the field of view, (c). The number of all cells in the field of view, d, and the number of multinucleate cells, c, are outputted as the result of analysis to the calculating unit, in which the rate of multinucleation is calculated.

In what follows, the present invention will be described in more detail with reference to Examples, which are not intended to restrict the invention.

EXAMPLES

Example 1. Treatment for Multinucleation

In order to examine the rate of multinucleation of sheet-shaped cell cultures of skeletal myoblasts, two kinds of sheet-shaped cell cultures (Sheet A and Sheet B) were prepared. The sheet-shaped cell cultures were examined for the rate of multinucleation according to the following protocol.

Each of the sheet-shaped cell cultures of skeletal myoblasts was subjected to an enzyme treatment, to be completely dissociated into mononuclear skeletal myoblasts. The skeletal myoblasts resulting from dissociation of Sheet A and Sheet B are designated respectively myo A and myo B. The dissociated cells were inoculated onto culture slides. The culture slides were placed in a $CO_2$ incubator. The cells were cultured under the conditions of 37° C. and 5% $CO_2$ for 14 to 22 hours.

After cultivation, the culture slides were removed from the $CO_2$ incubator and observed under a microscope and imaged by a digital camera. The number of multinucleate cells was counted, and the rate of multinucleation was calculated from the formula: (Number of multinucleate cells)/(Total number of cells)×100 [%]. Each cell is regarded as having one cytoplasm so long as the segments of cytoplasm are connected with one another, and each cell is regarded as one multinucleate cell if it contains two or more nuclei in one cytoplasm. (In FIG. 3, the regions surrounded by dotted lines.)

Example 2: Comparison of Cytokine Yielding Capacity

Subsequently, the two kinds of sheet-shaped cell cultures of skeletal myoblasts, Sheet A and Sheet B, were examined for the capacity of yielding cytokine by using the following measurement kits. Quantikine Human VEGF (made by R&D Systems Inc.), Quantikine Human CXCL 12/SDF-1α (made by R&D Systems Inc.), and RayBio Human HGF ELISA (RayBiotech, Inc.). Measurement was carried out according to the protocol specified by each kit.

Figure 2:
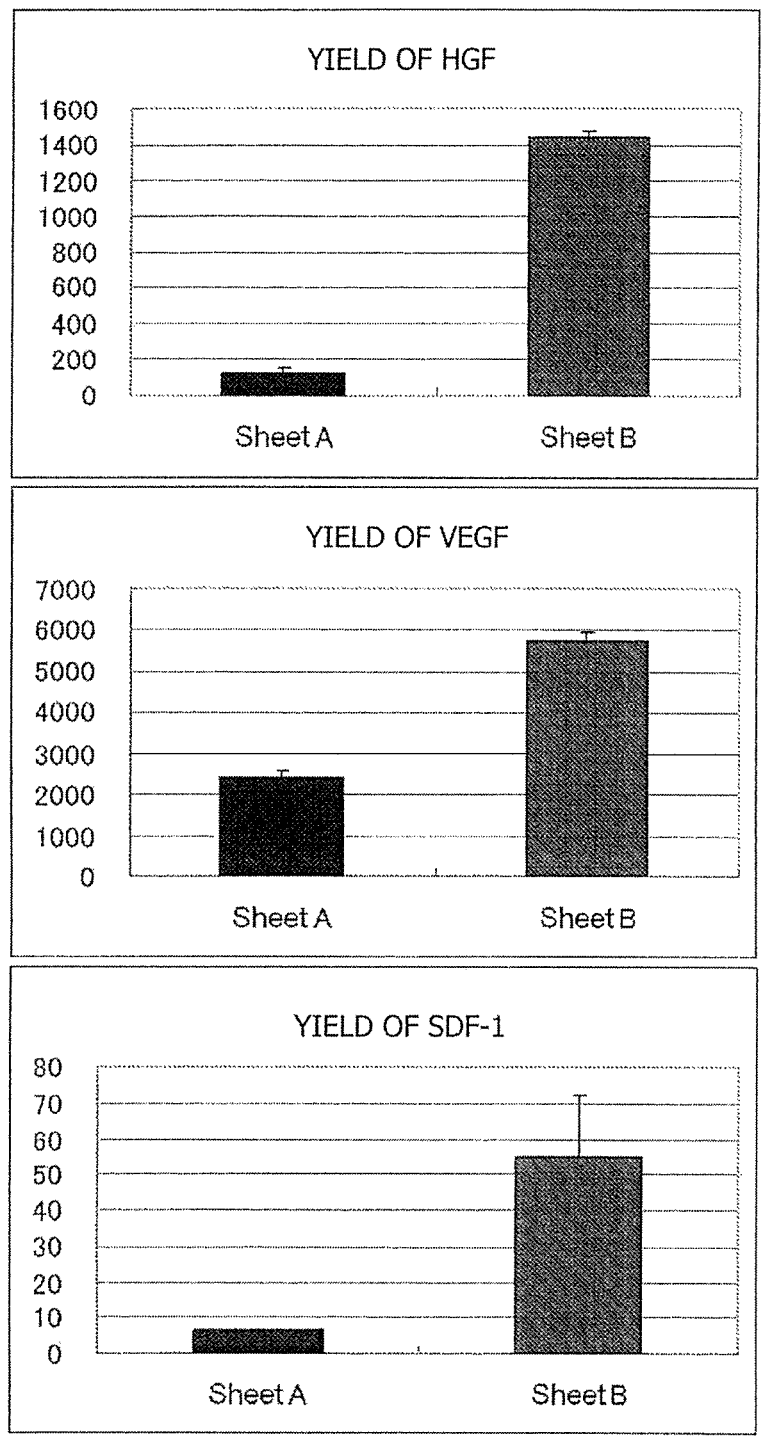
FIG. 2 is a diagram illustrating how two kinds of sheet-shaped cell cultures of skeletal myoblasts (sheet A and sheet B) composed of two kinds of skeletal myoblasts (myo A and myo B), respectively, different in rate of multinucleation, differ in the ability to yield cytokine. It is noted that Sheet B, which is composed of myo B having a higher rate of multinucleation, yields much more cytokine than sheet A, which is composed of myo A having a lower rate of multinucleation.

The results are shown in FIGS. 1 and 2. The rate of multinucleation is around 16.8% for myo A and around 29.6% for myo B (see FIG. 1). As regards the cytokine yielding capacity, Sheet B is much higher than Sheet A for HGF, VEGF, and SDF-1 (see FIG. 2). These species of cytokine are said to be concerned with the regeneration of cardiac muscle. The foregoing results suggest that Sheet B, which is composed of skeletal myoblasts myo B having a high rate of multinucleation, is more competent for transplantation to the heart than Sheet A.

As above-described, the use of the method according to the present invention has for the first time made it possible to evaluate the competence of grafts for transplantation. The result of evaluation helps improve the effect of treatment by transplantation.

The invention claimed is:

1. A method for identifying sheet-shaped graft samples that are competent for transplantation to a heart of a mammal, the method comprising:
    culturing cells of a mammal of interest to form sheet-shaped graft samples;
    treating a first portion of the sheet-shaped graft samples with an enzyme to dissociate the first portion of the graft samples into cells;
    culturing the dissociated cells for at least 14 hours;
    detecting a level of each of HGF, VEGF, and SDF-1 of at least a portion of the cultured dissociated cells prior to transplantation;
    comparing the detected level of each of HGF, VEGF, and SDF-1 from the cultured dissociated cells to a predetermined threshold level of each of HGF, VEGF, and SDF-1 relating to multinucleating ability associated with competence for transplantation;
    identifying the sheet-shaped graft sample as competent for transplantation to a heart of a mammal when the detected level of each of HGF, VEGF, and SDF-1 prior to transplantation is above the predetermined threshold level of each of HGF, VEGF, and SDF-1, or identifying the graft sample as not competent for transplantation to a heart of a mammal when the detected level of each of HGF, VEGF, and SDF-1 is below the predetermined threshold level of each of HGF, VEGF, and SDF-1, wherein a graft sample identified as competent for transplantation to a heart of a mammal has a higher detected level of each of HGF, VEGF, and SDF-1 than a graft sample identified as not competent for transplantation to a heart of a mammal; and
    after identifying the sheet-shaped graft samples as competent for transplantation, preparing a remaining non-dissociated second portion of the sheet-shaped graft samples for transplantation in sheet-shaped form in a heart of a mammal.

2. A method for improving the effect of treatment by graft transplantation to a heart of a mammal, the method comprising:
    culturing cells of a mammal of interest to form sheet-shaped graft samples;
    treating a first portion of the sheet-shaped graft samples containing cells with an enzyme to dissociate the first portion of the sheet-shaped graft samples into cells;
    culturing the dissociated cells for at least 14 hours;
    detecting a level of each of HGF, VEGF, and SDF-1 of at least a portion of the cultured dissociated cells prior to transplantation;
    comparing the detected level of each of HGF, VEGF, and SDF-1 from the cultured dissociated cells to a predetermined threshold level of each of HGF, VEGF, and SDF-1 relating to multinucleating ability associated with competence for transplantation;
    identifying the sheet-shaped graft sample as competent for transplantation to a heart of a mammal when the detected level of each of HGF, VEGF, and SDF-1 prior to transplantation is above the predetermined threshold level of each of HGF, VEGF, and SDF-1, or identifying the graft sample as not competent for transplantation to heart of a mammal when the detected level of each of HGF, VEGF, and SDF-1 is below the predetermined threshold level of each of HGF, VEGF, and SDF-1, wherein a graft sample identified as competent for transplantation to a heart of a mammal has a higher detected level of each of HGF, VEGF, and SDF-1 than a graft sample identified as not competent for transplantation to a heart of a mammal; and
    after identifying the sheet-shaped graft samples as competent for transplantation, administering a remaining non-dissociated competent sheet-shaped graft sample to a heart of a mammal in need thereof.

3. A method for improving the effect of treatment by graft transplantation to a heart of a mammal, the method comprising:
    obtaining a sheet-shaped graft sample that is one of a group of sheet-shaped graft samples prepared by culturing cells of a mammal of interest and that has been identified as competent for transplantation by detecting a level of each of HGF, VEGF, and SDF-1 in cultured dissociated cells from one of the group of the sheet-shaped graft samples prior to transplantation relating to a multinucleating ability of cells in the graft sample associated with competence for transplantation; and
    after identifying the group of sheet-shaped graft samples as competent for transplantation, administering a remaining non-dissociated competent sheet-shaped graft sample from the group of graft samples to a heart of a mammal in need thereof.

4. The method of claim 1, further comprising correlating a level of each of HGF, VEGF, and SDF-1 to multinucleating ability to provide the predetermined threshold level of each of HGF, VEGF, and SDF-1.

5. The method of claim 2, further comprising correlating a level of each of HGF, VEGF, and SDF-1 to multinucleating ability to provide the predetermined threshold level of each of HGF, VEGF, and SDF-1.

6. The method of claim 3, further comprising correlating a level of each of HGF, VEGF, and SDF-1 to multinucleating ability to provide the predetermined threshold level of each of HGF, VEGF, and SDF-1.

7. The method of claim 1, wherein the cells of the mammal of interest are skeletal myoblasts.

8. The method of claim 2, wherein the cells of the mammal of interest are skeletal myoblasts.

9. The method of claim 3, wherein the cells of the mammal of interest are skeletal myoblasts.

* * * * *